US005501974A

United States Patent [19]

Griffin

[11] Patent Number: 5,501,974

[45] Date of Patent: Mar. 26, 1996

[54] DISRUPTING A HYDROPHOBIC LAYER FORMED DURING FERMENTATION WITH NITROGEN DIOXIDE

[76] Inventor: David Griffin, 1 Paddington Cir., Broxville, N.Y. 10708

[21] Appl. No.: 416,925

[22] Filed: Apr. 4, 1995

Related U.S. Application Data

[63] Continuation of Ser. No. 186,060, Jan. 24, 1994, abandoned, which is a continuation of Ser. No. 896,419, Jun. 10, 1992, abandoned.

[51] Int. Cl.$^6$ .............................. C12N 1/38; C12N 1/14; C12P 1/04; C02F 3/02

[52] U.S. Cl. ............................ 435/244; 435/41; 435/170; 435/171; 435/243; 435/252.1; 435/254.1; 210/608; 210/631; 210/708; 210/710; 210/758

[58] Field of Search .................................... 435/244, 243, 435/252.1, 254.1, 170, 171, 41; 210/608, 631, 708, 710, 758

[56] References Cited

U.S. PATENT DOCUMENTS

| | | | |
|---|---|---|---|
| 4,280,818 | 7/1981 | Shulz et al. | 44/56 |
| 4,285,936 | 8/1981 | Pier et al. | 424/180 |
| 4,327,179 | 4/1982 | Moebus et al. | 435/42 |
| 4,390,624 | 6/1983 | Leavitt | 435/107 |
| 4,693,891 | 9/1987 | Collins et al. | 424/92 |
| 4,894,229 | 1/1990 | Polson et al. | 424/92 |

*Primary Examiner*—David M. Naff
*Assistant Examiner*—L. Blaine Lankford
*Attorney, Agent, or Firm*—Handal & Morofsky

[57] ABSTRACT

A process and apparatus for treating culture medium with a dilute acid such as nitric acid, are disclosed. In a preferred embodiment, nitric acid is sprayed on to a floating oily layer of hydrophobic materials at the surface of a stilled culture rich in aerobic bacteria, which materials can obstruct oxygen take up. The nitric acid surface treats the protective hydrophobic third phase, increasing its surface viscosity and the undesired lipid or oily materials to be readily removed mechanically. Oxygen take up and thence microorganismic growth are promoted. Quite small quantities of dilute acid are effective and leave no toxic residue. An optional embodiment entrains nitrogen dioxide in the aeration gases to form nitric acid in situ for surface treatment of thin oily films occluding bubbles in the culture broth.

5 Claims, 2 Drawing Sheets

Step 4
Skimming

Step 3
Agitation

DISRUPTING A HYDROPHOBIC LAYER FORMED DURING FERMENTATION WITH NITROGEN DIOXIDE

CROSS-REFERENCE TO RELATED APPLICATIONS

This application is a Continuation of application Ser. No. 08/186,060, filed 24 Jan. 1994, now abandoned, which was a continuation of 07/896,419, filed 10 Jun. 1992, now abandoned.

TECHNICAL FIELD

The present invention relates to interface mass transfer enhancement in multi-phase systems, especially the enhancement of gas or vapor mass transfer across an interface or boundary in a gas-liquid system. A particular field of application of the invention comprises processes and apparatus for the treatment of microbial or microorganism cultures to improve cultivation efficiency. Other fields include inorganic and organic process chemistry.

BACKGROUND

Useful industrial multi-phase processes frequently depend upon effective access of a consumable gaseous resource to an active liquid phase. In complex systems such, for example as a microorganismic culture medium, which is frequently an aqueous soup or broth, a third phase can be present which interferes with the mass transfer of such gaseous or vaporous resource across a gas-liquid interface. A typical undesired third phase is a hydrophobic slick or slime, rich in oils, greases or fats, which can coat the interface smothering and interfering with mass transfer.

Cultivation of microorganisms, or microorganisms, in tanks or vats, pipes and other process equipment is an important industrial activity responsible for the production inter alia of food supplements and pharmaceuticals. Industrial microbiological processes are carefully managed as to conditions of temperature, nutrient stock and residence time in order to optimize efficiency. Other precautions are commonly taken to prevent ingress of foreign organisms which might flourish in the nutrient-rich process broths employed, seriously contaminating them. In other words, the environment around the tanks is generally kept aseptic or sterile. Precise characterization and control of the process microorganisms is the norm in a well-developed and fastidious industry.

The present invention is particularly concerned with processes employing aerobic microorganisms, i.e. microorganisms, including bacteria and useful fungi such as yeasts, whose metabolic processes require the presence of oxygen, and are cultured in substantially aqueous growth media. Many such cultivation processes generate oily or greasy residues which rise to the surface of the process vessel and form a gas-transport inhibitive impermeable hydrophobic third phase in the form of a slick or film at the air-liquid interface. This hydrophobic third phase is a substantial barrier to oxygen access, inhibits microorganismic activity and greatly reduces process efficiency.

To improve aeration, and thence oxygen access to aerobic culture media, many and various agitation devices are customarily used. However, they do not destroy the hydrophobic third phase, so that aeration efficiency is still impaired. Mechanical removal of this hydrophobic third phase, for example by skimming, may reduce the third phase but is not effective in eliminating the smothering effect of the third phase. Also, skimming is difficult to execute effectively, especially in a vigorously agitated vessel, and wastes culture medium. Such mechanical treatments leave a hydrophobic residue to impede gas transport at the interface.

Because of his background and experience the present inventor is familiar with commercial processes involving major microfloral growths in the alien environment of sewage treatment.

The "Griffin Oxinite Process", Griffin Pollution Control Corporation, Yonkers, N. Y., (1970) discloses a process for the gaseous treatment of sewage with activated air, which is effective in reducing odor, crown corrosion and slime build up on superstructures. The activated air used in the "Oxinite" ("Oxinite" is a trademark of Griffin Pollution Control Corporation) process is prepared by subjecting air to electrical discharge and de-ozonization. Further benefits of the "Oxinite" process include humidity reductions, accelerated bacterial growth, grease reduction and the increase of dissolved oxygen in both gravity-fed and pumped sewage systems.

Kellum U.S. Pat. No. 3,344,061, assigned to Griffin Pollution Control Corporation, discloses a sewage treatment process similar to the "Oxinite" process and using de-ozonized activated air, which asserts the benefits of reduced biological demand, elimination of noxious odors and reduction of sulfide formation as well as reduction of dangerous methane generation.

Beyond harboring microorganisms, there is little to connect the fields of sewage treatment and the industrial culture of microorganisms. The one is a highly technical, controlled process employing specific or narrow-band worker microorganisms and conducted under conditions that accurately maintain preferred temperature and pH ranges and exclude ingress of undesired organisms that could rapidly multiply in the process soup, whereas the other is a low technology imprecise field rife with organisms of every description. The physical dispersion of the multi-phase constituents is also different including, in the case of sewage heterogenous solid-liquid mixtures and an interactive overhead environment.

Skilled workers in the art of industrial microbiology are not likely to perceive useful teachings to be obtainable from the art of sewage treatment: the arts are not analogous.

Other microrganismic processes to which the invention is applicable include processes employing anerobic organisms requiring a gaseous resource such as carbon dioxide, ammonia, methane or hydrogen sulfide. Worker microorganisms have utility not just for synthesis processes which yield a useful product such as a foodstuff or pharmaceutical, but also in digestive processes which breakdown undesired complex materials, such as sewage or cellulose into simpler, more readily disposable products.

In general, the invention is applicable to processes where the worker microorganisms are maintained in or dependent on a substantially aqueous phase.

SUMMARY OF THE INVENTION

Broadly stated, the invention comprises a multiphase industrial production or digestion process carried out in a multi-phase system, said multi-phase system comprising an active aqueous medium phase, said active aqueous medium maintaining an active agent to effect said production or digestion process, said active agent being dependent upon and consuming a gaseous resource, a gaseous phase including said gaseous resource and a third hydrophobic phase impeding access of said gaseous resource to said active aqueous medium, said gaseous phase and said aqueous medium phase having an interface across which said gaseous resource is supplied to said active agent, said process comprising applying a hydrophobic phase breakdown agent to said multiphase system to break down said third phase and enhance mass transfer of said gaseous resource across said interface to said active agent.

The invention, as claimed, is intended to provide a remedy. It solves the problem of how to provide a simple and effective process for treating microorganismic cultures which can improve the efficiency and economy of the process. The invention also solves the problem of providing simple and economic apparatus for carrying out such a treatment process.

A more specific object of the invention is to provide a microorganismic culture process in which oily or greasy hydrophobic third phases are broken up, reduced or destroyed and oxygen access is improved.

To meet these and other objects, the invention provides, in one aspect, an industrial microbiological process utilizing aerobic microorganisms said process comprising aerating a microorganism-rich aqueous culture medium in a process vessel wherein said process liberates hydrophobic materials to form a hydrophobic third phase in said culture medium, said hydrophobic third phase being of reduced gas permeability and impeding access of oxygen to said aerobic microorganisms which process further comprises applying a dilute acid to the hydrophobic third phase to dispel said hydrophobic third phase and improve microorganism productivity. Preferably, said acid is dilute nitric acid.

In another aspect, the invention provides a process in which dilute nitric acid is applied to surface layers of the hydrophobic materials by forming the nitric acid in situ from a nitrogen oxide gas. A readily available, or produced, sufficiently oxidized oxide of nitrogen is nitrogen dioxide which dissolves in water with the production of both nitrous and nitric acid species.

In a preferred embodiment, the inventive process breaks down or disrupts, and enables removal of, the smothering oily or hydrophobic barrier by means of a two-prong attack. On the one hand, a small amount of dilute nitric acid, the quantity being determined by the amount of hydrophobic material liberated, is applied to the stilled surface of the culture broth. In addition, a small amount of nitrogen dioxide is introduced into the airflow to react with water vapor or water to form nitric acid is situ and attacks any molecular oil or lipid barrier that may interfere with the transfer of oxygen at the bubble's surface.

BRIEF DESCRIPTION OF THE DRAWINGS

One way of carrying out the invention is described in detail below with reference to drawings which illustrate only one specific embodiment of the invention and in which.

BEST MODE FOR CARRYING OUT THE INVENTION

Figure 2:
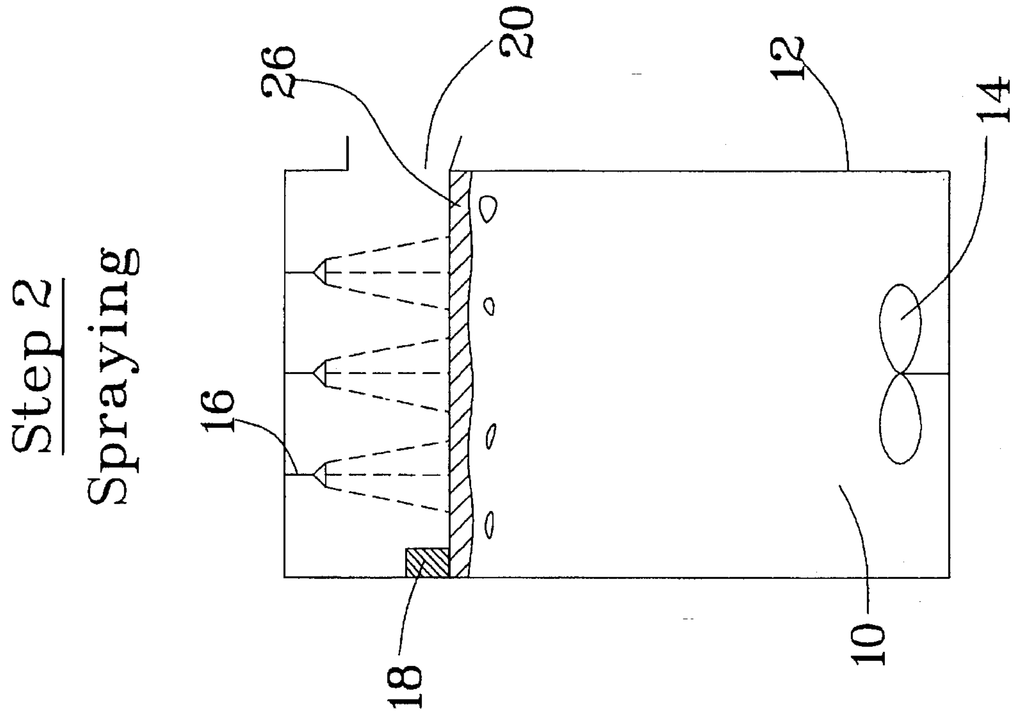
FIGS. 1 to 4 are schematic views of four stages of a microbial culture process according to the invention.

When microrganisms die, their cells disintegrate. Proteinaceous materials from the cell's interior tend to sink, while phospholipids and hydrophobic fatty acids float to the surface contributing to the formation of a slimy barrier phase. Dilute nitric acid is particularly effective in destroying or dispersing this phase because it is able not only to nitrify and solubilize many of the hydrophobic barrier consitituents, but also to oxidize them, breaking down larger molecules to less noxious forms and introducing solubilizing moieties such as —OH, =O, $—NO_2$, —COOH and more complex polar moieties and linking groups, all of which assist dispersal of the barrier and inhibit its interface smothering effects.

Microorganisms can also, while living, exude sticky films of polysachharide-based materials to help position themselves in a favorable environment. Such polysacharride-based films can be damaging contributors to a barrier phase.

In another aspect, the invention provides an industrial microbiological process utilizing aerobic microorganisms said process comprising aerating a microorganism-rich aqueous culture medium in a process vessel wherein said process liberates hydrophobic materials and said microorganisms discharge an adhesive polysaccharide exudant, said polysaccharide exudant mixing with and binding said hydrophobic materials to form a hydrophobic interface in said culture medium, said interface being of reduced gas permeability and impeding access of oxygen to said aerobic microorganisms which process further comprises applying a dilute acid to the hydrophobic third phase to disperse said hydrophobic third phase and improve microorganism productivity, said acid acting to hydrolyze said polysaccharide exudant to break down its adhesive properties.

If desired, the process can be supplemented by mechanical removal of hydrophobic materials. By means of my invention these materials are found to ball up or otherwise agglomerate and be much more readily removable. By breaking down the sticky sugars or slime exuded by the microorganisms, often for the purpose of clinging to fixed structures, the ability of the hydrophobic third phase to smother the culture medium and starve it of oxygen is greatly reduced.

Surprisingly, I have discovered that the strength and quantity of acid used can be very modest. It is not necessary to use a strength and quantity sufficient to hydrolyze all the hydrophobic material, and indeed, to do so could be damaging to the desired microorganisms, what appear to be adequate are the much lower quantities needed to break up the adhesive exudates (from the microorganisms) that hold the hydrophobic third phase together, often as a scum or slime.

Very often, the hydrophobic third phase tends to form on an upper surface of said culture medium in which case said acid is sprayed downwardly on to said upper surface.

A particularly advantageous acid is dilute nitric acid. The rate of application of said acid is related to the rate of take up of said acid by said hydrophobic third phase and is controlled to avoid a residual excess of acid. This can be done, for example, by monitoring the pH of the culture medium and controlling the rate of application of acid to maintain said pH.

Dilute nitric acid is particularly valuable because it is not only efficacious as an hydrophobic third phase dispersant, but also it can promote microorganism growth, especially growth of aerobic bacteria, because it provides a source of nitrogen. This works beneficially in a synergistic manner in that this very microorganism-consumability of nitric acid reaction products ensures that there are no harmful residues. Indeed, far from being harmful, recent research shows important roles for nitric oxide as a neurotransmitter.

In small quantities, oxidized sulfur and phosphorus are also biologically utilized, and should therefore also be compatible with and avoid leaving any harmful residue in the process end product or wastes.

In preferred embodiments, said acid is a dilute mineral acid of strength not greater than 0.1N, especially in a concentration of from 0.005 to 0.05N. Nitric acid is the most preferred embodiment because of its biological nutritive impact, in low concentrations, its oxidizing power and its unique and surprising ability to break up hydrophobic interface barriers. The latter can, perhaps, be explained, in part, by the readiness with which it will attack organics and the high water-solubility or hydrophilicity of its reaction products.

Low, non-lethal concentrations are adequate in a microorganismic culture environment, because the volume of barrier material will not usually be great. By contrast, prior art sewage treatment processes involve relatively high concentrations of fatty or oily materials, from human and industrial waste that would not be effectively dispersed with low concentrations of acid.

The dilute mineral acid can be selected from the group consisting of sulfuric acid, hydrochloric acid, phosphoric acid and nitrous acid.

Preferred culture media are rich in aerobic bacteria, however the invention is broadly applicable to culture media rich in many classes of microorganisms, for example microorganisms of a genus selected from the group consisting of STREPTOCOCCUS, STAPHYLOCOCCUS, SACCHAROMYCES, NEUROSPORA, PENICILLIUM, *ESCHERICHIA COLI,* KLEBSIELLA, NEISSERIA and LISTERIA. Some exemplary strains are *STAPHYLOCOCCUS AURES,* STREPTOCOCCUS ALPHA HEMOLYTIC and *F. MUCOR.*

Apparatus for industrial culture of microorganisms can, according to his invention, comprise a process vessel an aerator to aerate a culture medium rich in aerobic microorganisms and comprising an acid applicator for applying acid to said medium, said acid applicator being connected to a supply of aqueous dilute acid.

A preferred acid is a dilute mineral acid of strength not greater than 0.1N, although 0.01N, or less is preferred. Such very dilute mineral acid is relatively easily handled without requiring undue special measures. Although hydrochloric and sulfuric acids are applicable, the most preferred acid is dilute nitric acid. Nitrous acid could be used but is less practical. Both nitric and nitrous acids have the advantage of providing nitrogenous bacterial nutrients that promote the growth of preferred organisms. Other bulk acids such as phosphoric can be effective, but have one or another drawback such as causing environmental contamination.

Low molecular weight, biodegradable organic acids, for example acetic acid can also be used.

The inventive microorganismic cultures treatment process is surprisingly effective in improving the biotic character of the microorganismic cultures, in promoting desired bacterial growth, in increasing the dissolved oxygen content and in reducing odors. Especially important and surprising is that a simple application of dilute nitric acid is remarkably effective in dispersing grease, displaying an ability to ball-up surface layers of grease that normally accumulate on microorganismic cultures and improve the access of oxygen to the aqueous phase of the microorganismic cultures.

BEST MODE FOR CARRYING OUT THE INVENTION

In a preferred embodiment, acid applicators are distributed throughout a microorganismic cultures system wherever the microorganismic cultures microflora is protected from air by grease, or greasy or fatty, water-immiscible membranes and where it is practical to apply acid in dilute aqueous solution. In vivo bacterial colonies are known to manufacture sticky slimes which serve to anchor the colony and improve its exposure to nutrients. Such slimes are mixtures of carbohydrates and proteins and can also tend to isolate the bacterial colony from microorganismic cultures materials. Surprisingly, treatment with dilute acid is also effective in dispersing such slimes, improving admixture of the bacteria with microorganismic cultures and dissolved oxygen.

Break-up and dispersal of grease brought about by the acid treatment process of the present invention, greatly enhances other aeration processes including those incidental to turbulent aeration of volumes of microorganismic cultures in process plant. Such aeration is, of course, well known to cause accelerated action of aerobic microorganisms. As stated above, a preferred acid is nitric, which furnishes nitrogen, a biotic nutrient, to the microflora, and is economical and readily available. Nitric acid can be piped to the point of application or provided in tanks, mobile or stationary, or supplied as concentrated nitric acid and diluted in situ.

The concentration level of acid and its rate of application to the microorganismic cultures in the process vessel should be controlled to be adequate to produce a desired level of benefits, pursuant to the teachings of this invention, but not enough to kill significant quantities of beneficial bacteria. The acid is metered either locally at its discharge points or more centrally at distribution points or both so that its discharge can be quickly and accurately controlled. Clearly, actual rates of application will vary widely and depend upon factors such as the solids content or richness of the microorganismic cultures, their flow rate and surface area as well as their grease content and dissolved oxygen content.

For these reasons, preferred management practice is to monitor several parameters of the culture medium. Determination of dissolved oxygen, bacterial count by important genera or species, grease content and pH will provide a substantial data profile on which to predicate control of the rate or manner of application of acid to the culture medium. Of these parameters, the dissolved oxygen count is the most important and may be adequate alone.

The acid application rate is increased in response to low dissolved oxygen, high pH or high grease and decreased for low bacterial count, for low pH or when an optimal dissolved oxygen level is reached, as too high an oxygen content can be toxic.

More sophisticated control can be provided by building a historical database of these characteristics, statistically analyzing the data and relating it to anticipated culture medium process rate and composition characteristics known to, or generated by, management personnel to compile a predictive model of acid utilization. From experience, and records, management often has information as to load variations, which information can be utilized in a predictive model. The processing of this data would of course be computerized. Employing servo-operated metering devices to apply acid to the culture medium, and by controlling it from a central processor, the acid treatment process can be automated to run in accordance with feedback of the above-described control parameters or said predictive model. Such an automated system preferably includes a data entry station and is programmed to be operable in a mode accepting manually entered acid demand parameters.

As stated above, the acid applicators are structured to apply acid to the surface of the culture medium where grease is present or is expected to be present and can include accurate metering means. A number of applicator stations is located throughout the system and can be managed to fire streams of acid, preferably nitric acid, periodically on to the aerated culture medium at intervals judged to provide complete coverage of the culture medium, after allowing for its agitation by turbulent flow.

The acid can be sprayed or dripped on to moving culture medium. Overhead spray nozzles are used with multiple divergent orifices arranged in a pattern to spread the acid across the surface of the culture medium body. A preferred spray pattern extends over the complete surface of the process vessel.

Installation of spray heads over the process vessel is effected by attachment to any convenient superstructure, or where none such exists, by providing appropriate dependent or uprising support structure.

However much aeration they receive, aerated bodies of culture medium still contain fats, oils or grease and benefit from active treatment to promote grease dispersal and break down thereby to enhance oxygen transfer and promote favorable aerobic bacterial activity. Quite remarkably the process of the invention can cause grease slicks on culture medium to roll up into balls that have a spongy character resembling rendered fat and are easily dispersed.

NEW TEXT ADDED DECEMBER 1993

While not being limited to any particular theory of operation, the inventive process of applying dilute acid topically to hydrophobic, or oily by-products of fermentation processes, is believed to be effective partially to oxidize the oils, primarily at the exposed surfaces of any oily droplets or films. Superficial oxidation attacks the oil's characteristic film-forming tendency that enables an oil to spread out to a molecular thickness, in favorable circumstances. It is this characteristic of oil that the inventive process attacks and disrupts. Superficial hydrolysis and oxidation of hydrophobic bodies renders surface areas hydrophilic and tacky, increasing apparent viscosity and disrupting the ability of the oils to spread.

Surface treatment with nitric acid

In one preferred embodiment, the inventive process is practiced in the following steps:

1) A rolling body of liquid microbiological culture broth is stilled for a period of time sufficient to allow a substantial, oily film to float to the surface, and preferably substantially to cover the surface. Desirably, the majority of the oils (or fatty, or hydrophobic or lipid material) is allowed to rise to the surface. This quiescent interlude may be from two to sixty minutes, preferably from five to fifteen minutes, and its duration is chosen to optimize lipid removal with minimal interruption of the culture process.

2) Dilute nitric acid is then applied topically, for example by spraying directly on to the oily film, keeping the broth stilled.

3) Agitation to roll the body of culture broth is resumed leading to agglomeration of hydrophobic materials into solid or semi-solid masses, lumps or balls.

4) The rolling body is again stilled, as in 1). Now the agglomerated masses, lumps or balls of hydrophobic material rise to the surface during the still period. The risen, agglomerated masses are mechanically removed, for example by skimming.

5) Commencing with step 2, steps 2)–4) are repeated at intervals throughout the duration of the culture process, the length of the intervals being determined by the rate of formation of hydrophobic materials.

This process is illustrated schematically in FIGS. 1–4. In each figure, a culture broth 10 is contained in a vessel equipped with an agitator 14, overhead spray nozzles 16 a movable skimmer 18 and a lipid discharge port 20.

Figure 1:
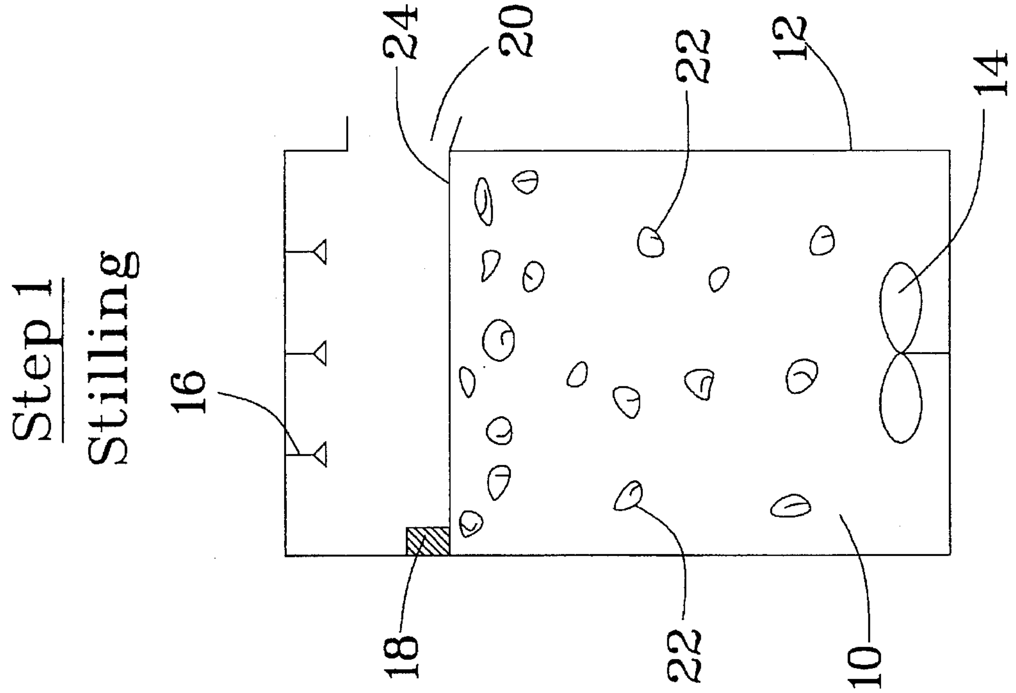

FIG. 1 illustrates step 1 "STILLING" in which the broth 10, is stilled as shown by the the stationary agitator 14, and lipids 22 are rising to the surface 24 of the broth.

FIG. 2 illustrates step 2 "SPRAYING" in which nitric acid is sprayed through nozzles 16 on to a layer 26 of accumulated lipid.

Figure 3:
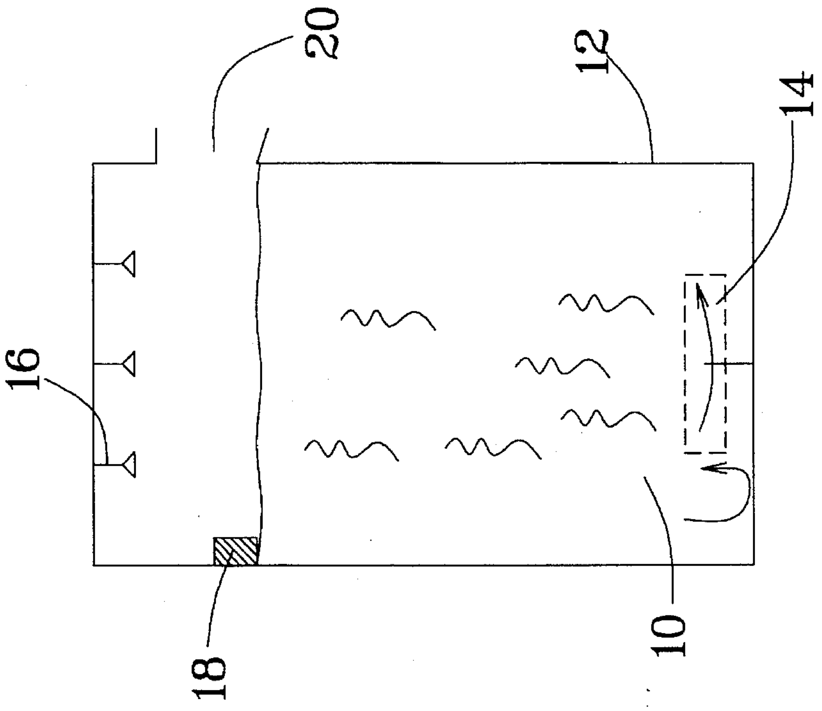

FIG. 3 illustrates step 3 "AGITATION", or the normal culturing condition, in which agitator 14 is actuated creating a rolling broth in which small nitric-treated lipid masses come into contact with one another and agglomerate into larger masses or balls.

Figure 4:
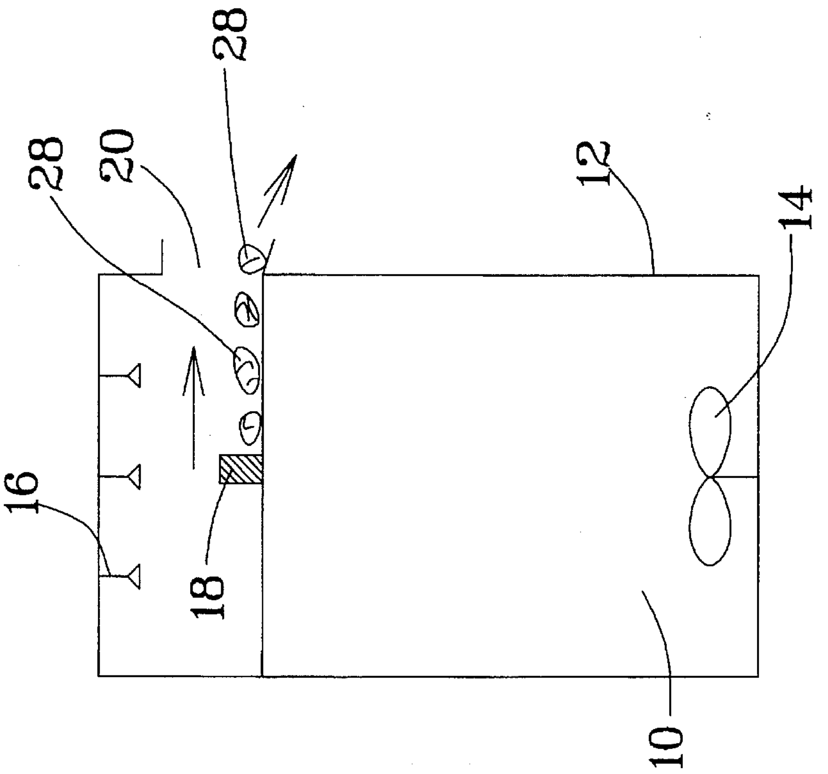

FIG. 4 illustrates step 4 "SKIMMING" in which the broth 10, is again stilled as shown by the the stationary agitator 14, and risen lipid masses 28 are collected by movable skimmer 18 advancing across the surface of the broth to discharge the risen lipid masses 28 out through discharge port 20.

By spraying nitric acid, or other dilute mineral acid, on to the upwardly exposed surface layers of the risen oily film, only a portion of the oily or hydrophobic material is contacted by, and chemically altered by the nitric acid. Nitric acid is not intimately admixed with and distributed throughout the culture broth, but is sprayed, or otherwise applied to the surface of the broth when that surface is still and covered, or substantially covered by an oily risen film. In this way, little, if any applied nitric acid finds its way into the broth.

Possible reaction mechanism

Again, the present invention is not bound by any particular theory as to its operation, nevertheless, my understanding of how the beneficial results provided by the invention is as follows. It appears that the above-described nitric acid attack on the surface-treated portion of the hydrophobic oils renders the surface layers hydrophilic and gives those layers a more viscous quality. They become tacky or sticky acquiring a viscous adhesiveness. This superficial viscous adhesiveness is used, in the method of the invention to strip or scour other untreated oils out of suspension in the broth and into agglomerates, when the operator starts the rolling aeration process again.

An objective is to use the roll together with the viscous adhesiveness of the surface-treated oils to encapsulate other oily materials in suspension, producing solid, semisolid or spongy balls or masses that can be easily skimmed or otherwise removed from the culture vessel at the next stilling period. Although some culture bacteria may be captured the masses of formed balls of fat, such loss is minor and is more than offset by the improved transfer of oxygen, or aeration that is achieved by eliminating oily materials from the medium.

The purpose of aeration and the diffusion of air/oxygen is to get the largest possible air-to-liquid surface area. This is often accomplished through the use of diffusers that producing multitudes of tiny bubbles. Generated and entrapped in a rolling liquid broth, the detention time of the air bubbles is optimized.

The total surface area of the bubbles and their number are of great importance to the transfer of air or oxygen into solution in the liquid phase of the broth to be available to bacteria. Residence time is an important factor in the economics of the culture process meaning that the stripping of the oily hydrophobic materials from the culture medium is of major importance. The oily materials, if allowed to remain, create a non-pervious molecular barrier around the air bubbles and substantially reduce air-transfer efficiency thereby severely suppressing the growth process in the culture medium.

Entraining nitrogen dioxide

In another embodiment of the invention, dilute nitric acid is applied to surface layers of the hydrophobic materials by forming the nitric acid in situ from a nitrogen oxide gas. A readily available, or produced, sufficiently oxidized oxide of nitrogen is nitrogen dioxide which dissolves in water with the production of both nitrous and nitric acid species.

By entraining a small amount of nitrogen dioxide, for example from 1 to 10 and preferably from 2 to 5 percent by volume, into the air or oxygen flow just prior to diffusing the air or oxygen into the culture medium, small quantities of nitric acid can be delivered precisely where it is most likely to be needed, at the surface the bubble makes with the culture medium, where any oily interface that may be present to inhibit oxygen take up, can be attacked by the in situ nitric acid and can be removed by dispersal to another location.

Furthermore, the nitrogen dioxide can be expected to generate nitric acid in the bubble in the vapor phase by reaction with water vapor within the bubble as the bubble is formed. The small amount of nitric acid formed is presciently located within the bubble to attack any thin, near-molecular film of oil or other lipids that may be coating the bubble's surface, opening the film and allowing a more efficient transfer of air or oxygen to the culture medium.

Preferably, the amount of nitrogen dioxide added is a maintenance level applied in small amounts such that any nitrogen dioxide not absorbed and escaping is negligible.

Clearly nitrogen dioxide entrainment can be combined with the first embodiment process of topical application of dilute nitric acid to the stilled broth. In this case, the entrained nitrogen dioxide serves to reduce the amount of dilute nitric acid needed during the stilling periods.

The inventive concepts

The invention can be better understood when it is realized that low viscosity oils, which can be liberated in a culture medium, can spread to a thin film of molecular thickness on an aqueous substrate. Even a molecular thickness of oil is enough seriously to impede the efficient transfer of air or oxygen into the aqueous bacterial phase. Thus small quantities of oil can substantially suppress bacterial growth.

Thus, in its preferred embodiment, the inventive process breaks down or disrupts, and enables removal of, this smothering oily barrier by means of a two-prong attack. As described herein, a small amount of dilute nitric acid, the quantity being determined by the amount of hydrophobic material liberated, is applied to the stilled surface of the culture broth. In addition, a small amount of nitrogen dioxide is introduced into the airflow to react with water vapor to form nitric acid that attacks any molecular oil or lipid barrier that may interfere with the transfer of oxygen at the bubble's surface.

The objective of the invention is not further to diffuse and disperse the oils into a suspension which would be self-defeating, further increasing their surface area. Nor is the objective to remove the oily materials by hydrolyzing them and converting them to water-soluble materials, for that would require large quantities of nitric acid, and would generate substantial quantities of materials potentially harmful to the bacteria. Rather the objective is chemically to treat the oily interface to render it easily removed from the culture medium, using innocuous agents and conditions. This is achieved using a minimum of nitric acid and nitrogen dioxide in combination and in separate phases to attack and break up the oily interface. The treated surfaces become viscous and sticky, enabling the remaining oil or lipids to be agglomerated and or encapsulated during the aeration step of the operation.

Surprisingly, the conditions required for bacterial culture are favorable to the chemistry of the inventive process. Hydrolysation of nitrogen oxides to nitric acid, and the desired lipid oxidation and hydrolysis processes, proceed rapidly at moderate temperatures in the range of from 10° C. to 70° C., which range includes the temperatures within a degree or two of 37° C., preferred for bio-mass culture media.

Both nitric acid and nitrogen dioxide are active oxidants at these moderate temperatures. They readily react with either the liquid or vapor state of water to produce active oxidizing and hydrolyzing moieties.

Enriching the air flow into the culture medium with oxygen, can enhance both oxygenation of the culture and surface treatment of the hydrophobic interface.

Preheating aeration gases

Since gases when released from compression have a marked drop in temperature, before being introduced into the gas flow, nitrogen dioxide and any oxygen are preferably preheated by approximately 10° C. or alternatively, the mixed gas stream can be mildly preheated before introduction into the culture broth. Thus, the temperature of the entrained gases can be adjusted to control the culture medium temperature. By employment of suitable temperature sensors in the medium, use of gas-heating (or gas cooling means) means and suitable electronic or microprocessor control means, temperature control of the broth by means of the introduced gas temperature can be automated.

Such preheating provides the benefits of avoiding loss of temperature of the culture medium slowing the bio-mass growth and life cycle and of helping optimize the chemical reactions of the inventive process.

Balancing cooling due to expansion of the pressurized aeration gases against the exothermic culture process, an optimal aeration gas temperature will usually be a few degrees Centigrade, from about 1 to 10 and preferably from about 2 to about 5 degrees, below the desired culture broth temperature. For a culture broth operating at or near 37° C., one preferred aeration gas temperature is 35° C.

Dilute nitric acid is a powerful oxidizing agent, the nitrogen atom of which is subject to valence changes. In general, the more dilute the nitric acid, the greater the change in the valence of nitrogen. Also, the more active the reducing agent or oxidizable species with which the nitric acid reacts, the greater is the change in the valence of nitrogen.

Further concepts and apparatus

Thus, in the inventive process, dilute nitric acid is sprayed specifically only on the surface of floating oil or lipid materials, being mechanically directed to target the floating masses or films. As optimum efficiency is obtained, the volume of the lipid materials reduces, the reduction proceeding more rapidly if nitrogen dioxide is introduced into the aeration gas. Preferably mechanical means are employed to avoid spraying nitric acid directly on to the aqueous or bacterial phase of the culture medium, as the volume or area of surface lipid shrinks. This can be achieved at the simplest level by terminating spraying when the surface film breaks up. Alternatively, spraying can be redirected, or its coverage reduced to target the shrunken lipid area.

One embodiment of lipid breakup and removal apparatus, intended to be operative primarily while the broth is stilled, comprises a skimming boom movable across the surface of the broth to contain the lipid materials and, preferably to discharge them into a collection vessel. By carrying spray nozzles on the boom directed towards the lipid confinement area, discharge of nitric acid directly behind the advancing skimming boom can be prevented.

However process conditions will vary with different cultures and it is desirable to treat with nitric acid any oil or lipid layer that may remain on the surface after skimming off agglomerated balls or masses of fats that have developed during a prior aeration period.

As will be apparent to those skilled in various arts, beneficial applications of the inventive process are not limited only to culture mediums, but the above-described techniques for the continuous removal of oily or greasy phases liberated in oxygen-consuming aqueous industrial processes can be applied in other fields.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. An industrial microbiological process utilizing aerobic microorganisms said process comprising employing an air or oxygen stream to aerate a microorganism-rich aqueous culture medium in a process vessel with the production of air bubbles in said culture medium, said culture medium comprising an aqueous phase and a microorganism phase, wherein said process forms a hydrophobic third phase in said culture medium, said hydrophobic third phase being of reduced gas permeability and impeding access of oxygen to said aerobic microorganisms which process further comprises forming dilute nitric acid in situ to facilitate dispersion of said hydrophobic third phase by entraining nitrogen dioxide gas in said air or oxygen stream in quantities sufficient to break down its binding properties and permit agglomeration and dispersal of said hydrophobic third phase materials, said quantities being controlled to prevent toxicity to said microorganisms due to said nitric acid being introduced to said culture medium.

2. A process according to claim 1 wherein from 1 to 10 percent by volume of nitrogen dioxide is entrained into said air or oxygen stream just prior to diffusing the air or oxygen into the culture medium.

3. A process according to claim 1 wherein the amount of nitrogen dioxide entrained is maintained such that any nitrogen dioxide not absorbed and escaping is negligible.

4. A process according to claim 1 wherein said nitrogen dioxide entrainment is combined with topical application of dilute nitric acid to a fermenting culture medium or broth, the entrained nitrogen dioxide serving to reduce the amount of dilute nitric acid employed topically during fermentation.

5. A process according to claim 1 wherein said air stream is enriched with oxygen.

* * * * *